United States Patent
Lamichhane et al.

(10) Patent No.: US 9,273,341 B2
(45) Date of Patent: Mar. 1, 2016

(54) METHODS FOR TREATMENT OF BACTERIAL INFECTIONS

(71) Applicants: THE JOHNS HOPKINS UNVIERSITY, Baltimore, MD (US); INSTITUT NATIONAL DE LA SANTÉ ET DE LA RECHERCHE MÉDICALE, Paris (FR)

(72) Inventors: Gyanu Lamichhane, Towson, MD (US); William R. Bishai, Towson, MD (US); Radhika Gupta, Baltimore, MD (US); Marie Lavollay, Bourg la Reine (FR); Jean-Luc Mainardi, Chaville (FR); Michel Arthur, Arcueil (FR)

(73) Assignees: The Johns Hopkins University, Baltimore, MD (US); Institut National de la Sante et de la Recherche Medicale, Paris (FR)

( * ) Notice: Subject to any disclaimer, the term of this patent is extended or adjusted under 35 U.S.C. 154(b) by 42 days.

(21) Appl. No.: 14/222,338

(22) Filed: Mar. 21, 2014

(65) Prior Publication Data
US 2014/0342364 A1 Nov. 20, 2014

Related U.S. Application Data

(63) Continuation of application No. 13/283,406, filed on Oct. 27, 2011, now abandoned.

(60) Provisional application No. 61/407,256, filed on Oct. 27, 2010.

(51) Int. Cl.
| | |
|---|---|
| *A01N 43/00* | (2006.01) |
| *A61K 31/33* | (2006.01) |
| *C12Q 1/18* | (2006.01) |
| *A61K 31/00* | (2006.01) |
| *A61K 31/424* | (2006.01) |
| *A61K 31/43* | (2006.01) |
| *A61K 45/06* | (2006.01) |
| *C12Q 1/37* | (2006.01) |
| *C12Q 1/68* | (2006.01) |

(52) U.S. Cl.
CPC . *C12Q 1/18* (2013.01); *A61K 31/00* (2013.01); *A61K 31/424* (2013.01); *A61K 31/43* (2013.01); *A61K 45/06* (2013.01); *C12Q 1/37* (2013.01); *C12Q 1/689* (2013.01); *C12Q 2600/136* (2013.01); *C12Q 2600/158* (2013.01)

(58) Field of Classification Search
None
See application file for complete search history.

(56) References Cited

FOREIGN PATENT DOCUMENTS

WO WO 2007014951 A2 * 2/2007

OTHER PUBLICATIONS

Lavollay et al., "The Peptidoglycan of Stationary-Phase *Mycobacterium tuberculosis* Predominantly Contains Cross-Links Generated by L,D Transpeptidation," Journal of Bacteriology, Jun. 2008, p. 4360-4366.*
Wietzerbin et al. "Occurrence of D-alanyl-(D)-meso-diaminopimelic acid and meso-diaminopimelyl-meso-diaminopimelic acid interpeptide linkages in the peptidoglycan of Mycobacteria" *Biochemistry*, 13:3471-3476 (1974).
Lavollay et al. "The peptidoglycan of stationary-phase *Mycobacterium tuberculosis* predominantly contains cross-links generated by L,D-transpeptidation" *Journal of Bacteriology*, 190: 4360-4366 (2008).
Hugonnet et al., "Meropenem-clavulanate is effective against extensively drug-resistant *Mycobacterium tuberculosis*" *Science*, New York, NY, 323, 1215-1218 (2009).
Fauci, A.S., "Multidrug-resistant and extensively drug-resistant tuberculosis: the National Institute of Allergy and Infectious Diseases Research agenda and recommendations for priority research" The Journal of infectious diseases 197, 1493-1498; (2008).
Gandhi et al., "Extensively drug-resistant tuberculosis as a cause of death in patients co-infected with tuberculosis and HIV in a rural area of South Africa" *Lancet*, 368:1575-1580; (2006).
Jindani, A. et al., "Bactericidal and sterilizing activities of antituberculosis drugs during the first 14 days" American journal of respiratory and critical care medicine 167; 1348-1354; 2003.
Wayne, L.G., et al. "Nonreplicating persistence of *Mycobacterium tuberculosis* " Annual review of microbiology 55; 139-163; 2001.
Betts et al., "Evaluation of a nutrient starvation model of *Mycobacterium tuberculosis* persistence by gene and protein expression profiling" *Molecular microbiology* 43:717-731 (2002).
Voskuil et al. "Inhibition of respiration by nitric oxide induces a *Mycobacterium tuberculosis* dormancy program" *The Journal of experimental medicine* 198:705-713 (2003).
Keren et al., "Specialized persister cells and the mechanism of multid rug tolerance in *Escherichia coli* " *Journal of bacteriology* 186:8172-8180 (2004).
Vollmer, The architecture of the murein (peptidoglycan) in gram-negative bacteria: vertical scaffold or horizontal layer(s)? *Journal of bacteriology* 186, 5978-5987 (2004).
Lamichhane et al., "A postgenomic method for predicting essential genes at subsaturation levels of mutagenesis: application to *Mycobacterium tuberculosis* " Proceedings of the National Academy of Sciences of the United States of America.
Mainardi et al., "A novel peptidoglycan cross-linking enzyme for a beta-lactam-resistant transpeptidation pathway" *The Journal of biological chemistry* 280:38146-38152 (2005).

(Continued)

*Primary Examiner* — Craig Ricci
*Assistant Examiner* — Jared D Barsky
(74) *Attorney, Agent, or Firm* — DLA Piper LLP (US)

(57) ABSTRACT

The peptidoglycan layer is a vital component of the bacterial cell wall, which comprises 4→3 and 3→3 transpeptide cross-linkages, the formation of which are catalyzed by D,D- and L,D-transpeptidases, respectively. Methods for the treatment of bacterial infections with agents that inhibit L,D-transpeptidases, either alone or in combination with D,D-transpeptidase inhibitors, are provided herein. Also provided are methods for the treatment of chronic stage tuberculosis with agents that inhibit enzyme with L,D-transpeptidase activity.

10 Claims, 7 Drawing Sheets

(56) References Cited

OTHER PUBLICATIONS

Lavollay et al., "The beta-lactam-sensitive D,D-carboxypeptidase activity of Pbp4 controls the L,D and D,D transpeptidation pathways in Corynebacterium jeikeium" *Molecular microbiology*, In press (2009).

Mainardi et al., "Unexpected inhibition of peptidoglycan LD-transpeptidase from Enterococcus faecium by the beta-lactam imipenem" *The Journal of biological chemistry* 282:30414-30422 (2007).

Hugonnet et al., "Irreversible inhibition of the *Mycobacterium tuberculosis* beta-lactamase by clavulanate" Biochemistry, 46:11998-12004 (2007).

Ghuysen, J.M., Serine beta-lactamases and penicillin-binding proteins. Annual review of microbiology 45:37-67 (1991).

Waxman et al., "Penicillin-binding proteins and the mechanism of action of beta-lactam antibiotics" *Annual review of biochemistry*, 52:825-869 (1983).

Besra, G., "Preparation of cell wall fractions. in Mycobacteria Protocols" (eds. Parish, T. & Stoker, 457 N.G.) 91-107 (Humana Press, Totowa, 1998).

Wiegand et al., "Agar and broth dilution methods to determine the minimal inhibitory concentration (MIC) of antimicrobial substances" *Nature protocols* 3(460)163-175,(2008).

Crick et al., "Biosynthesis of the arabinogalactan-peptidoglycan complex in The Mycobacterial Cell Envelope", *Glycobiology*, 11(9):107R-118R(2001).

Amrein et al., "Purification and characterization of recombinant human p50csk protein-tyrosine kinase from an *Escherichia coli* expression system overproducing the bacterial chaperones GroES and GroEL" *Proceedings of the National Academy of Sciences of the United States of America*, 92:1048-1052 (1995).

Auger et al., "A MurG assay which utilises a synthetic analogue of lipid I", *FEMS microbiology letters*, 219:115-119 (2003).

Arbeloa et al.,"Synthesis of mosaic peptidoglycan cross-bridges by hybrid peptidoglycan assembly pathways in gram-positive bacteria", *J Biol Chem*, 279:41546-41556 (2004).

Valway et al., "An outbreak involving extensive transmission of a virulent strain of *Mycobacterium tuberculosis*", *The New England journal of medicine*, 338:633-639 (1998).

Lee et al., "Site-specific integration of mycobacteriophage L5: integration-proficient vectors for *Mycobacterium smegmatis, Mycobacterium tuberculosis*, and bacille Calmette-Guerin", *Proceedings of the National Academy of Sciences of the United States of America*, 88:3111-3115 (1991).

Gupta et al., "The *Mycobacterium tuberculosis* gene, $Idt_{Mt2}$, encodes a non-classical transpeptidase required for virulence and resistance to amoxicillin", *Nat Med*, 16(4):449-469 (2010).

Templin et al., "A defect in cell wall recycling triggers autolysis during the stationary growth phase of *Escherichia coli*", *The EMBO Journal*, 18(15):4108-4117 (1999).

Donald et al., "Early Bactericial Activity of Amoxicillin in Combination with Clavulanic Acid in Patients with Sputum Smear-positive Pulmonary Tuberculosis", *Scand J Infect Dis* 33:466-469 (2001).

Nadler et al., "Amoxicillin-clavulanic acid for treating drug-resistant *Mycobacterium tuberculosis*", *CHEST*, 99(4):1025-1026, 1991.

\* cited by examiner

| β-lactams (average mass) | | Observed | Increase in mass |
|---|---|---|---|
| None | (NA) | 39,049.94 | NA |
| Imipenem | (299.09) | 39,349.03 | 298.75 |
| Meropenem | (383.15) | 39,433.09 | 383.26 |
| Ertapenem | (475.14) | 39,525.08 | 475.03 |

FIG. 9

METHODS FOR TREATMENT OF BACTERIAL INFECTIONS

CROSS REFERENCE TO RELATED APPLICATION(S)

This application is a continuation of U.S. application Ser. No. 13/283,406, filed Oct. 27, 2011, which claims the benefit of priority under 35 U.S.C. §119(e) to U.S. Provisional Application Ser. No. 61/407,256, filed Oct. 27, 2010. The disclosure of each of the prior applications is considered part of, and is incorporated by reference in, the disclosure of this application.

GRANT INFORMATION

This invention was made in part with government support under NIH Grant No. AI30036. The United States government has certain rights in this invention.

BACKGROUND OF THE INVENTION

1. Field of the Invention

The invention relates generally to methods for treating bacterial infections by inhibition of L,D-transpeptidases and more specifically to methods for treating tuberculosis by inhibiting a *Mycobacterium tuberculosis* L,D-transpeptidase.

2. Background Information

Tuberculosis (TB) continues to be a major public health threat around the world The estimate that more lives will be lost in 2009 due to TB than in any year in history is alarming. An increasing number of cases reporting infection with multi- (MDR) and extensively drug-resistant (XDR) strains of *M. tuberculosis* has diminished our capability to respond effectively against this threat. A recent study reporting high mortality rates of patients co-infected with HIV and XDR-TB illustrates the need for new drugs to treat TB. It is speculated that poor patient compliance to treatment regimen, as the current therapy requires a combination of drugs to be taken daily for 6 months or more, is a major reason for emergence of drug resistance in TB. While >99% of *M. tuberculosis* bacilli are killed within 2 weeks of therapy, it takes the remainder of the therapy to effectively kill the surviving population. These bacilli, broadly termed 'persisters', are able to transiently tolerate drugs. The phenomenon of persistence is poorly understood. In vitro models designed to mimic the physiology of persisters are based on exposure to nitric oxide and depletion of oxygen and nutrients as these conditions are thought to prevail in a persisting infection in vivo.

A higher percentage of bacilli are able to survive exposure to drugs at stationary phase compared to exponential phase of growth. The bacterial cell wall, as an interface between the pathogen and the host, regulates diffusion, influx and efflux of drugs and metabolites. Integrity and permeability of this interface is highly significant to effective targeting of *M. tuberculosis* with drugs. Little is known about changes in the cell wall during chronic phase of infection and whether it regulates persistence of *M. tuberculosis* in the host. The mechanism by which *M. tuberculosis* maintains 3→3 cross-linkages in the peptidoglycan layer is poorly understood. An understanding of the factors involved in the regulation of cell wall physiology is crucial for developing drugs that effectively target and kill the persisters by interfering with this process.

SUMMARY OF THE INVENTION

The present invention is based on the seminal discovery of an *M. tuberculosis* gene, $ldt_{Mt2}$, encoding for an L,D-transpeptidase and identification of its role as a catalyst for the formation of non-classical 3→3 cross-linkages in the peptidoglycan layer. Inactivation of $ldt_{Mt2}$ and loss of the MT2594 protein results in altered colony morphology, attenuation in growth, loss of virulence, and increased susceptibility to β-lactams and β-lactamase inhibitors in vitro and during the chronic phase of tuberculosis infection as demonstrated in the mouse model of the disease. Non-classical 3→3 cross-linkages predominate the transpeptide networking of the peptidoglycan layer of non-replicating *Mycobacterium tuberculosis*. The peptidoglycan network is a dynamic structure that is cross-linked by both 4→3 and 3→3 transpeptide linkages. Both L,D- and D,D-transpeptidases are involved in the maintenance and remodeling of the peptidoglycan network in *M. tuberculosis*.

A method for treating a subject having a bacterial infection is provided herein. The method includes administering to a subject in need thereof an effective amount of an agent that inhibits L,D-transpeptidase activity, thereby treating the bacterial infection. In one aspect, the bacterial infection is caused by a Gram-negative bacterium. In another aspect, the bacterial infection may be caused by a Gram-positive bacterium.

In certain aspects, the bacterial infection is tuberculosis. In one aspect, tuberculosis is caused by a mycobacterial strain, including but not limited to, *Mycobacterium tuberculosis*. In another aspect, tuberculosis is chronic stage tuberculosis. In one embodiment, the L,D-transpeptidase is encoded by *Mycobacterium tuberculosis* gene $ldt_{Mt2}$.

In other aspects, the method further includes administering at least one antibiotic including, but not limited to, D,D-transpeptidase inhibitors or β-lactams, such as, amoxicillin. In yet other aspects, the method further comprises administering a β-lactamase inhibitor including, but not limited to clavulanic acid or a salt thereof.

BRIEF DESCRIPTION OF THE DRAWINGS

FIG. 1 depicts *M. tuberculosis* morphology and growth in vitro. A. shows images of the morphologies of wild-type *M. tuberculosis* (WT), LdtMt2 mutant (MUT) and the complemented strain (COMP) on solid media after 21 days of growth at 37° C. B. is a graphic representation of the growth of wild-type *M. tuberculosis* (WT), $Ldt_{Mt2}$ mutant (MUT) and the complemented strain (COMP) in Middlebrook 7H9 liquid medium at 37° C.

FIG. 2 illustrates characterization of $Ldt_{Mt2}$ from *M. tuberculosis*. A. is a schematic representation of domain composition of L,D-transpeptidases from *E. faecium* ($Ldt_{fm}$) and *M. tuberculosis* ($Ldt_{Mt2}$). Residues 250-377 of $Ldt_{Mt2}$ share homology with the catalytic domain of $Ldt_{fm}$ (Domain II, 338-466). B. is a photograph of a gel that shows purification of a soluble fragment of $Ldt_{Mt2}$ produced in *E. coli*. C. shows a mass spectrum with structure and inferred fragmentation pattern of the peptidoglycan dimer formed in vitro by $Ldt_{Mt2}$. The ion at m/z 974.51 was generated by losses of the two GlcNAc-MurNAc residues following fragmentations of the ether links connecting the lactoyl group to the C-3 position of MurNAc. Loss of each sugar decreased the m/z by 203. Cleavage of additional peptide bonds from the ion at m/z 974.51 gave ions at 703.36, 532.28, 433.22 and 272.15 as indicated in the inset. D. Is a bar graph that depicts the transcription profile of $Ldt_{Mt2}$ (MT2594) and $Ldt_{Mt1}$ (MT0125). RNA isolated from wildtype Mtb cultures at growth phases T1 ($A_{600\ nm}$=0.2), T2 ($A_{600\ nm}$=0.5), T3 ($A_{600\ nm}$=0.8), T4 ($A_{600\ nm}$=0.9), T5 ($A_{600\ nm}$=01.9), T6 ($A_{600\ nm}$=3.0), T7 (2 days post $A_{600\ nm}$=3.0) and T8 (3 days post clumping).

FIG. 3 is a graphic representation that illustrates assessment of growth, virulence and susceptibility to amoxicillin in vivo. A. shows bacterial burden in the lungs of three groups of mice, 28 per group, infected with wild-type *M. tuberculosis* (WT), Ldt$_{Mt2}$ mutant (MUT) or the complemented (COMP) strain. Bacterial burden in the lungs of mice in each infection were determined by plating lung homogenates onto Middlebrook 7H11 medium and enumerating colony forming units after 21 days of growth at 37° C. B. Three groups of mice, twelve per group, were infected with wild-type *M. tuberculosis* (WT), Ldt$_{Mt2}$ mutant (MUT) or the complemented (COMP) strain. The graph shows virulence of each strain was assessed by determining time-to-death following infection of mice with the three strains. C. Schematically represents the following timeline. Mice were infected with an aerosol of either WT or the strain lacking Ldt$_{Mt2}$ (MUT). Four mice from each infection group were sacrificed at 0, 1, 2, and 4 weeks following treatment, lungs were obtained and bacterial load was determined by enumerating colony forming units from lung homogenates cultured on Middlebrook 7H11 medium. D-F graphically represent a treatment regimen of the mice as follows. Following two weeks of infection, mice were treated daily with either no drug placebo as shown in D, or 25 mg/kg isoniazid as shown in E or 200 mg/kg amoxicillin or 50 mg/kg clavulanate as shown in F.

FIG. 6 is a series of bar graphs illustrating the transcription profile of Ldt$_{Mt2}$ (MT2594) and putative L,D-transpeptidases. RNA isolated from wild-type Mtb cultures at growth phases T1 (A$_{600\,nm}$=0.2), T2 (A$_{600\,nm}$=0.5), T3 (A$_{600\,nm}$=0.8), T4 (A$_{600\,nm}$=0.9), T5 (A$_{600\,nm}$=01.9), T6 (A$_{600\,nm}$=3.0), T7 (2 days post 3.0) and T8 (3 days post clumping). cDNA was prepared, quantified by qPCR and normalized to SigA. Note that the scale for Y-axis, which denotes expression relative to SigA, is different for each gene as ldt$_{Mt2}$ (MT2594) expression is many folds higher than that of its putative paralogs.

FIG. 8 illustrates the composition of the peptidoglycan of *M. tuberculosis* strain lacking MT2594. A. is a rp-HPLC profile of peptidoglycan fragments obtained by digestion of the peptidoglycan prepared from stationary phase cultures of MT2594 mutant with muramidases and treatment with ammonium hydroxide. mAU, absorbance unit×10$^3$ at 210 nm. B. is a table showing peptidoglycan composition: the relative abundance (%) was calculated by integration of the absorbance. $^a$Mass, observed monoisotopic mass. NA: not applicable; ND: not determined. E: D-iGlu. D-Lac: D-lactate; GlcNAc-MurNGlyc$^{anh}$; N-acetylglucosamine-anhydro-N-glycolylmuramic acid; mDap: meso-diaminopimelic acid; mDap$_{NH2}$: mDap with an amidated e carboxyl group.

DETAILED DESCRIPTION OF THE INVENTION

The peptidoglycan layer is a vital component of the bacterial cell wall. The existing paradigm describes the peptidoglycan network as a static structure that is cross-linked predominantly by 4→3 transpeptide linkages. However, the non-classical 3→3 linkages predominate the transpeptide networking of the peptidoglycan layer of *M. tuberculosis* during stationary phase of growth and possibly during infection in vivo. The molecular basis of these linkages, their significance to the physiology of the peptidoglycan layer, virulence and susceptibility of *M. tuberculosis* to drugs remain hitherto undefined. As disclosed herein, MT2594 (Rv2518c) has been identified as an L,D-transpeptidase that generates 3→3 linkages in *M. tuberculosis*. The loss of this gene was found to result in altered colony morphology, attenuation of growth, loss of virulence and increased susceptibility to a moxicillin/clavulanate during the chronic phase of infection. This suggests that 3→3 cross-linking is vital to the physiology of the peptidoglycan layer. Although a functional homolog exists, expression of MT2594 was found to be dominant throughout the growth phases of *M. tuberculosis*. The 4→3 transpeptide linkages are targeted by one of the most widely used classes of antibacterial drugs in human clinical use today, namely β-lactams. Recently, meropenem/clavulanate was shown to be effective against drug resistant *M. tuberculosis*. The results presented herein suggests that a combination of L,D-transpeptidase inhibitor and β-lactams could effectively target persisters during chronic phase of TB.

The cell wall of *M. tuberculosis* accounts for up to 40% of cell's dry mass compared to 5% and 10% in gram-positive and negative bacteria. It is approximated that the degree of peptidoglycan cross-linking is ~50% in *E. coli* whereas it is ~70-80% in *Mycobacterium* spp. Mycobacterial peptidoglycan layer is cross-linked with both 4→3 and 3→3 linkages. It was recently shown that 80% of the transpeptide linkages in the peptidoglycan of *M. tuberculosis* at stationary phase are of the non-classical 3→3 type. Described herein is identification of a gene (MT2594) that encodes an L,D-transpeptidase implicated in the synthesis of non-classical 3→3 peptidoglycan cross-linkages. Inactivation of MT2594 has been found to result in altered colony morphology, attenuation of persistence, and increased susceptibility to amoxicillin/clavulanate both in vitro and in the mouse model of TB.

Figure 1:
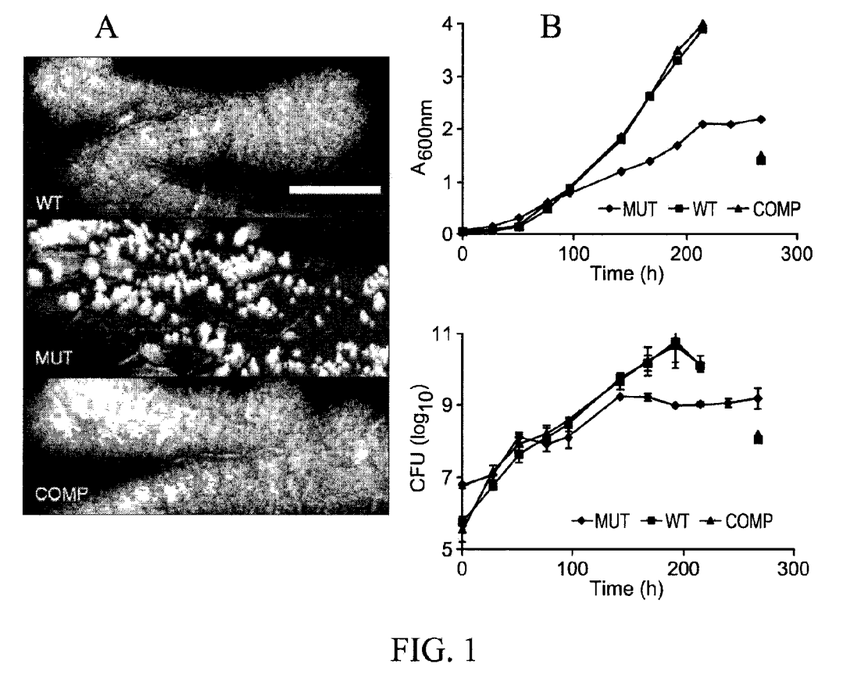

A mutant *M. tuberculosis* resulting from inactivation of gene MT2594 (Rv2518c), hereinafter referred to as ldt$_{Mt2}$, was isolated by screening a collection of 5,100 unique transposon insertion mutants for growth attenuation. Colonies of this mutant (ldt$_{Mt2}$::Tn) were smaller, smooth and had punctuated aerial growth rather than the typical large, rough and laterally diffuse morphology observed in the parent strain (FIG. 1a). The wild-type phenotype was restored upon complementation of the strain with a single copy of the gene, which was inserted at the chromosomal attB site. In liquid broth, culture of the mutant strain reached lower optical and cell densities compared with the parental strain (FIG. 1b). Complementation restored wild-type growth in the mutant. The ratio of colony forming units (CFU) of the mutant to WT at the beginning of the growth assay was 10:1 whereas after 192 hours it was 1:100. This indicates a 1000-fold larger increase in the wild-type population over 192 hours compared to the mutant strain. The doubling times of 18.1, 14.5 and 14.8 hours were derived from CFU data for the mutant, wild type and the complemented strains, respectively.

Figure 5:
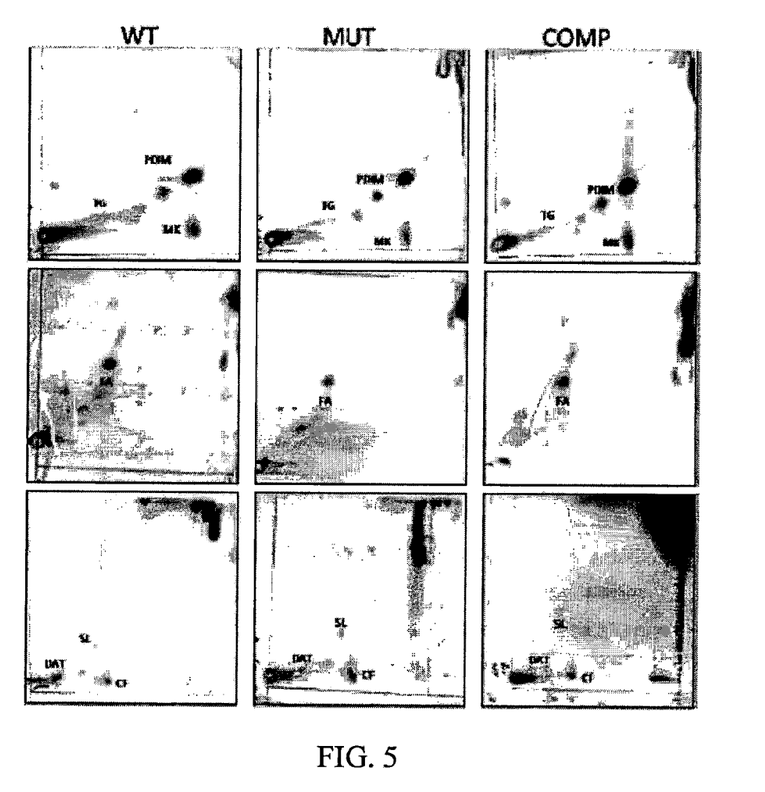
FIG. 5 is a series of photographs of thin layer chromatography (TLC) plates that depict characterization of lipid composition of the cell wall of wild-type, Ldt$_{Mt2}$ mutant (MUT), and the complemented strain (COMP) using TLC. Triacyl glycerol (TG), Pthiocerol dimycolates (PDIM), Meanquinones (MK), Free fatty acid (FA), Diacyltrehalose (DAT), Sulpholipids (SL), Cord factor (CF).

The outer layer of the cell wall consists of a thick layer of complex lipids. To account for the colony morphology phenotype, the composition of lipids in the mutant was examined. However, no change or difference in the composition of major cell wall lipids, namely triacyl glycerols, pthiocerol dimycolates, menaquinones, free fatty acids, diacyl trehalose, sulfolipids and cord factor, among the wild-type, mutant and the complemented strains was detected (FIG. 5).

Figure 2:
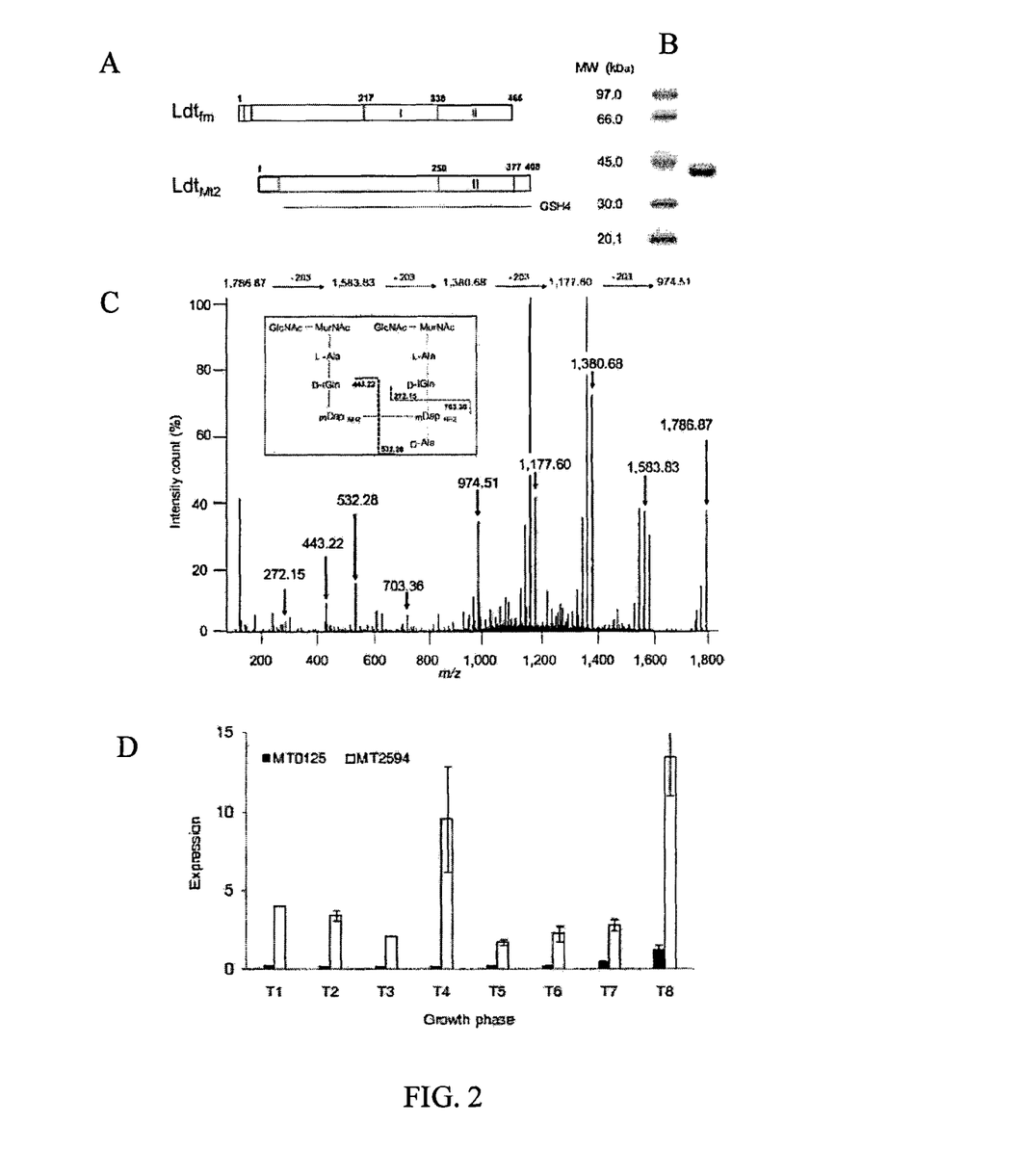

MT2594 ($Ldt_{Mt2}$) was initially annotated as a hypothetical protein with an unknown function. The N-terminus contains a putative single transmembrane domain spanning residues (positions 20-42) anchoring the remainder of the protein that is predicted to protrude outside the cell membrane into the cell wall. The C-terminal region of MT2594 is similar to the catalytic domain of the prototypic peptidoglycan L,D-transpeptidase from Enterococcus faecium (29% identity over 127 amino acids) including the active site cysteine residue within the invariant SHGC (SEQ ID NO:1) motif (FIG. 2a). To determine if $Idt_{Mt2}$ encodes a functional L,D-transpeptidase, a soluble fragment of the protein in Escherichia coli that was produced, purified and assayed for in vitro cross-linking activity (FIG. 2b). The substrate was a disaccharide-tetrapeptide monomer isolated from the peptidoglycan of Corynebacterium jeikeium, which has the same structure as the predominant monomer of M. tuberculosis. Electrospray mass spectrometry analysis of the reaction products revealed the formation of a peptidoglycan dimer (m/z=1, 786.87 $[M+H]^+$, inset in FIG. 2c) from two disaccharide-tetrapeptide monomers (m/z=938.44 $[M+H]^+$). Tandem mass spectrometry of the dimer (FIG. 2c) confirmed the presence of a 3→3 cross-link connecting two meso-diaminopimelic acids at the third position of the stem peptides. $Ldt_{Mt2}$ did not catalyze formation of dimers with disaccharide-peptide containing a stem penta peptide. Thus, $Ldt_{Mt2}$ was specific for stem tetrapeptides comparable to $Ldt_{Mt1}$ and the prototypic L,D-transpeptidase from E. faecium. These results demonstrate that MT2594 is an L,D-transpeptidase that catalyzes formation of 3→3 peptidoglycan cross-links.

Figure 6:
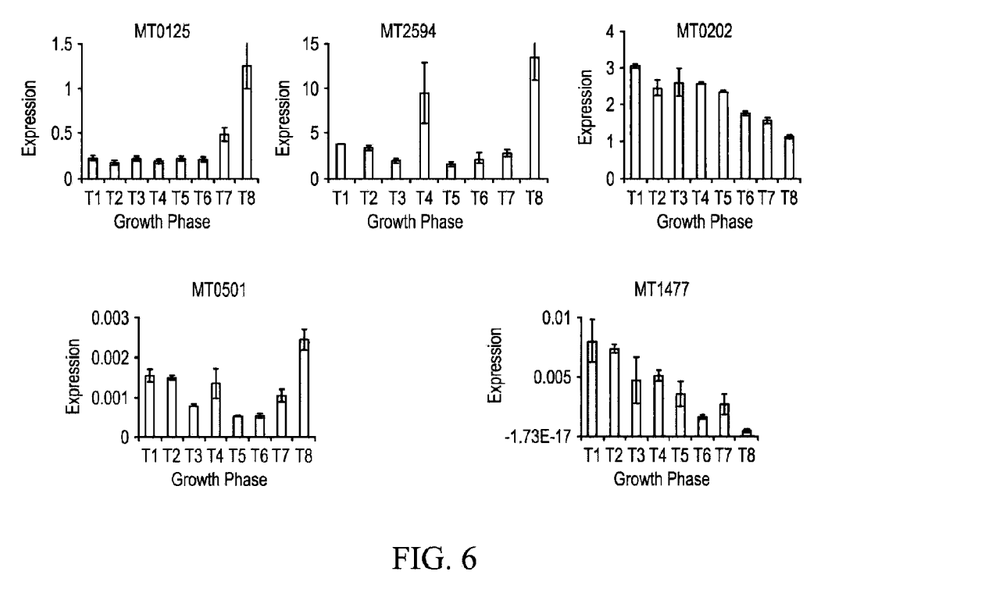
Figure 7:
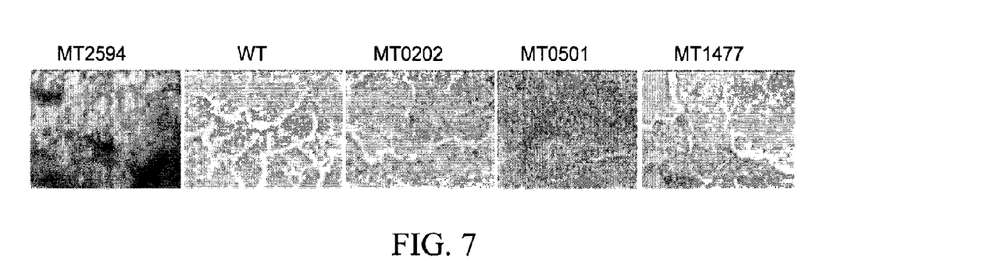
FIG. 7 is a series of photographs that show the morphologies of Ldt$_{Mt2}$ mutant (MT2594), parent *M. tuberculosis* wild-type strain (WT), MT0202, MT0501, and MT1477 mutants on Middlebrook 7H11 solid medium at 37° C. after 3 weeks of growth.
Figure 8:
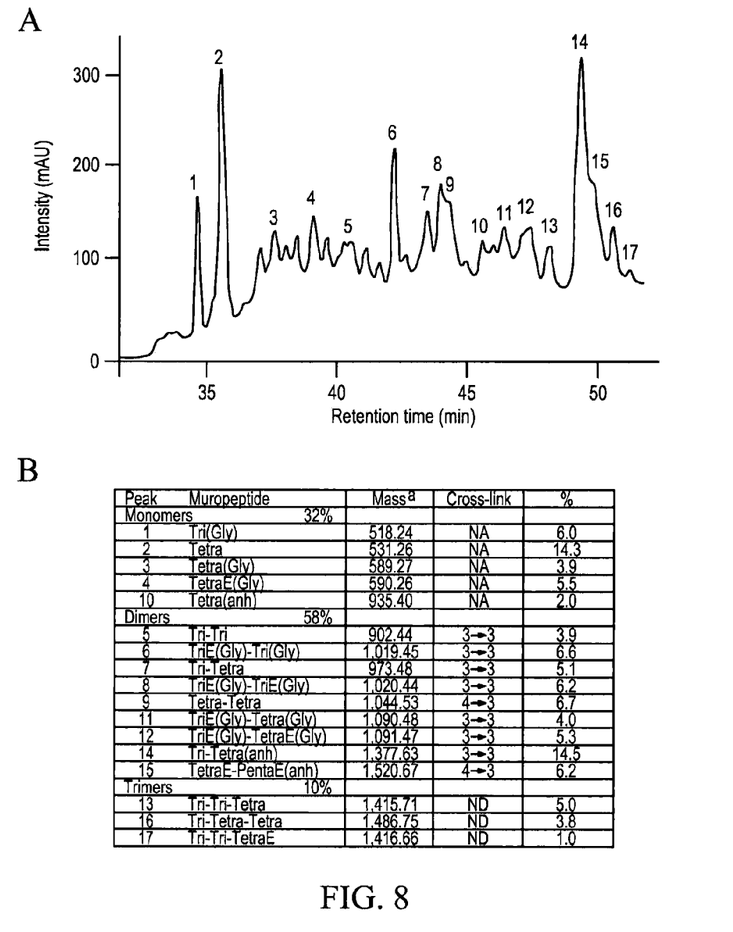
Figure 9:
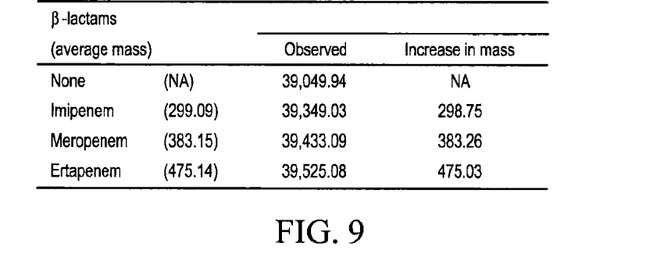
FIG. 9 is a table that demonstrates formation of adducts between Ldt$_{Mt2}$ and carbapenems. Ldt$_{Mt2}$ (5 μM) was incubated without antibiotic or with various carpapenems (50 μM). Proteins and adducts were detected by electrospray mass spectrometry. NA, not applicable; Adducts were not detected with ceftriaxone and ampicillin.

Further investigation revealed four putative paralogs of $Idt_{Mt2}$ in the genome of M. tuberculosis (MT0125, MT0202, MT0501 and MT1477). To gain an insight into the level of expression of the five paralogs, quantitative RT-PCR analyses on eight RNA samples prepared from exponential and stationary phases of growth (FIG. 6) was performed. The $Idt_{Mt2}$ mRNA was at least 5-fold more abundant than the combined expression of the remaining four paralogs. Next, the functional relevance of the paralogs to L,D-transpeptidation was assessed. M. tuberculosis mutants lacking MT0202, MT0501 and MT1477 had morphologies and growth phenotypes similar to that of the parent wild-type strain (FIG. 7). MT0202, MT0501 and MT1477 were purified, but L,D-transpeptidase activity using the peptidoglycan precursor as the substrate was not detected (Lavollay, M., unpublished results). MT0125 of M. tuberculosis strain (CDC1551 is identical to Rv0116c of strain $H_{37}Rv$, a gene designated $Idt_{Mt1}$ that was recently shown to also encode a peptidoglycan L,D-transpeptidase. Between the two L,D-transpeptidases, MT2594 was expressed at a level at least 10-fold higher than that of $Idt_{Mt1}$ at all phases of growth (FIG. 2d). The morphology, growth and virulence deficient phenotype of the $Idt_{Mt2}$ mutant indicates that low-level expression of $Idt_{Mt1}$ did not compensate for the loss of the L,D-transpeptidase activity of MT2594 although analysis of the peptidoglycan structure showed that 3→3 cross-linkages were synthesized by $Ldt_{Mt1}$ in stationary phase culture of the mutant (FIG. 8).

Imipenem (30 µM) abolished formation of $mDap^3$→$mDap^3$ cross-links by $Ldt_{Mt2}$. $Ldt_{Mt2}$ was not inhibited by ampicillin and by the third-generation cephalosporin ceftriaxone up to concentrations of 5,700 and 360 µM, respectively. Incubation of $Ldt_{Mt2}$ with imipenem, meropenem and ertapenem resulted in the formation of covalent adducts (Table S1). The average mass of the adducts matched the sum of average masses of $Ldt_{Mt2}$ and of the different carbapenems. No adduct was detected for ampicillin and ceftriaxone. Thus, $Ldt_{Mt2}$ was specifically inactivated by carbapenems as previously described for $Ldt_{Mt1}$ of M. tuberculosis and $Ldt_{fm}$ of E. faecium.

Figure 3:
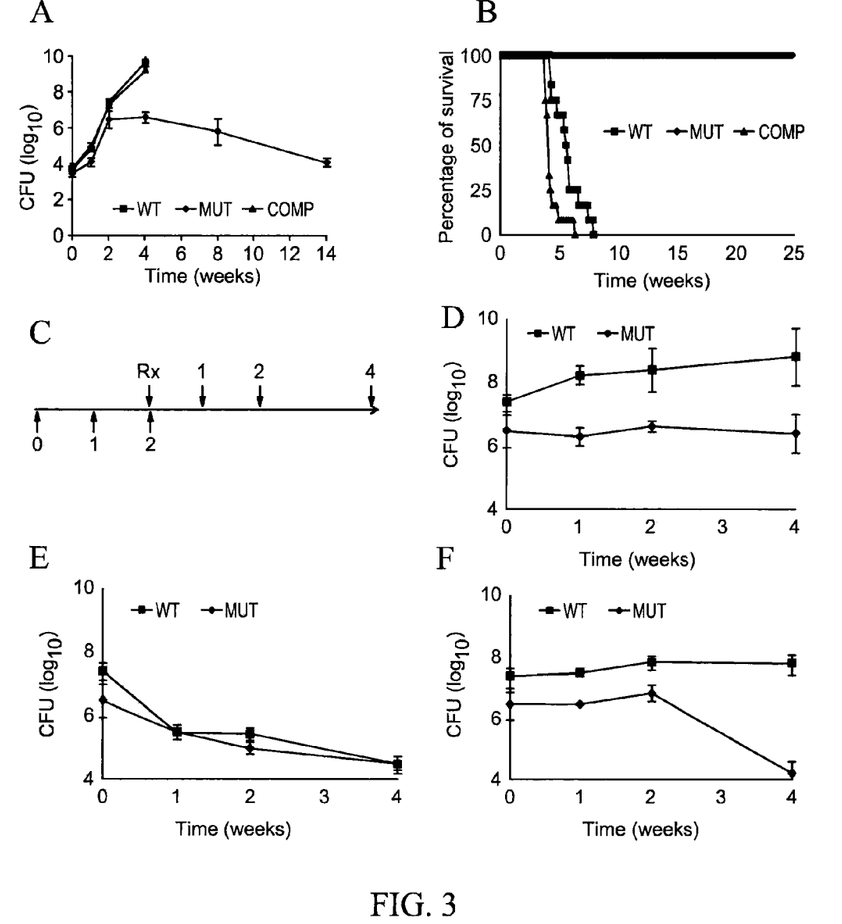

It was next assessed whether inactivation of $Ldt_{Mt2}$ affected in vivo growth and virulence of M. tuberculosis. Approximately 3.5 $log_{10}$ of CFUs of each strain was implanted in the lungs of three groups of immunocompetent Balb/C mice. The mutant established infection and exhibited a normal growth pattern during the first two weeks but discontinued proliferation at this stage of infection (FIG. 3a). The wild-type and the complemented strains proliferated rapidly until 4 weeks of infection, at which stage a heavy bacterial burden led to death of the animals (FIG. 3b). The median survival time for the wild-type and complement infected group were 38 and 30 days, respectively. The mice infected with the mutant strain did not die and signs of morbidity were not observed, despite the presence of approximately $10^4$ CFU in the lungs (FIG. 3a).

The non-classical 3→3 linkages comprise the majority of the transpeptide linkages in non-replicating M. tuberculosis. It is reasonable to expect that the loss of $Ldt_{Mt2}$ may compromise the mutant's ability to adapt during the chronic phase of infection, a critical stage in the pathogenesis of tuberculosis. If the failure in adaptation is the result of a defect in peptidoglycan cross-linking by $Ldt_{Mt2}$, another consequence could be an increased susceptibility to β-lactams. This hypothesis was tested by assessing susceptibility of the $Ldt_{Mt2}$ mutant to amoxicillin. M. tuberculosis produces a β-lactamase that is inactivated by clavulanic acid. The MIC of the commercial clavulanic acid-amoxicillin combination (Augmentin®) was 1.2 and 0.14 µg/ml for wild-type and the mutant strain respectively. Loss of MT2594 did not alter susceptibility to isoniazid (MIC=0.03 µg/ml) and D-cycloserine (5 µg/ml). Thus, loss of $Ldt_{Mt2}$ was associated with increased susceptibility to amoxicillin in the presence of clavulanic acid that inhibited the β-lactamase.

Susceptibility of the mutant strain to amoxicillin in the mouse was next assessed. Mice infected with either the wild-type M. tuberculosis or the mutant strain were treated daily with either phosphate buffered saline (PBS) as a placebo or 25 mg/kg of isoniazid or 200 mg/kg amoxicillin in combination with 50 mg/kg clavulanate. Isoniazid was similarly effective against both wild-type and the mutant strain (FIG. 3D-F). Bacterial burden in mice infected with the wild-type strain treated with amoxicillin/clavulanate was similar to the group that received placebo. Amoxicillin/clavulanate was ineffective during the first two weeks of treatment in mice infected with the mutant as the bacterial burden remained unchanged. However, a decrease of more than 2 $log_{10}$ in CFU was observed between 2 and 4 weeks of treatment demonstrating that the mutant is selectively susceptible to amoxicillin/clavulanate during the chronic phase of infection.

Figure 4:
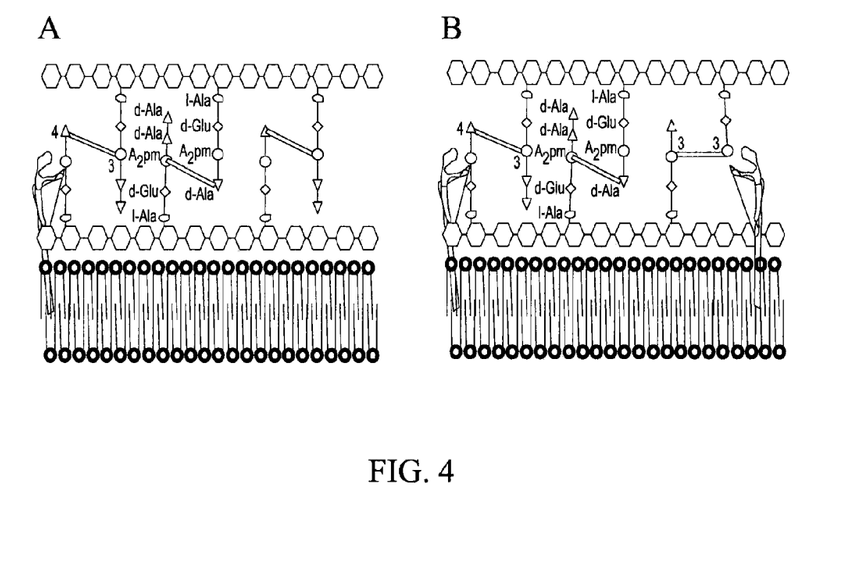
FIG. 4 is a schematic representation of the proposed model for physiology of the peptidoglycan layer in *M. tuberculosis*. A. shows the classical model of peptidoglycan crosslinking containing 4→3 inter peptide bonds. B. depicts the model based on recent data: the peptidoglycan is cross-linked with classical 4→3 and non-classical 3→3 inter peptide bonds. Both 4→3 and 3→3 transpeptidases are involved in maintenance and remodeling of the peptidoglycan layer in the proposed model

All bacteria possess an elaborate peptidoglycan layer in their cell wall. Many consider it a bacterial 'organelle' that is vital to the structure and physiology of the cell. It is generally thought that there are many similarities in biosynthesis of peptidoglycan layer between *E. coli* and *M. tuberculosis* including the production of precursors containing meso-diaminopimelic acid (mDAP) at the third position of stem peptides. In *E. coli* the main inter-peptide cross-linking occurs between the penultimate D-alanine (D-ala) at the fourth position of the donor and mDAP at the third position of the acceptor. Formation of this 4→3 bond is catalyzed by the D,D-transpeptidases that are the essential target of β-lactam antibiotics. The drugs are structural analogs of the D-Ala-D-Ala extremity of the peptidoglycan precursors and act as suicide substrate in an acylation reaction that irreversibly inactivate the enzymes. *E. coli* has served as the model organism for studying peptidoglycan metabolism but the existing paradigm built on this organism is incomplete. In this classical model, the peptidoglycan layer is regarded as a static network involving polymerization of glycan chains and cross-linking of adjacent chains by formation of 4→3 peptide bonds (FIG. 4A). Based on the data presented herein, a model describing the peptidoglycan layer as a dynamic structure whose inter-peptide linkages are altered as an adaptive response to a change in the environment and growth phase is proposed (FIG. 4B). The peptide chains are linked with both 4→3 and 3→3 bonds.

In addition to transpeptidases, endo- and carboxypeptidases are also present in bacteria and function to modify the peptidoglycan network. These enzymes have yet to be definitively identified in *M. tuberculosis*. A recent report showed gene pgdA to encode an N-deacetylase that is involved in modification of the peptidoglycan layer in *L. monocytogenes*. A putative homolog of pgdA exists in *M. tuberculosis*. This gene, MT1128 (Rv1096), has yet to be characterized and its in vivo function identified. Although MT2594 is a 3→3 transpeptidase, its loss and accompanying changes in the cross-linking may have pleiotropic effects on the metabolism of the peptidoglycan layer.

A novel molecular basis of 3→3 linkages and their physiological role for viability and virulence of *M. tuberculosis* has been demonstrated. MT2594 is an L,D-transpeptidase enzyme, which catalyzes formation of 3→3 linkages in the peptidoglycan of *M. tuberculosis* that is required for virulence and responsible for resistance of the pathogen. It has been shown that L,D-transpeptidation is required to resist killing by amoxicillin/clavulanate and that inhibition of $Ldt_{Mt2}$ alone may be sufficient to target the 3→3 linkages despite presence of redundancy. It may be inferred from these findings that both 3→3 and 4→3 transpeptide linkages need to be destroyed to effectively kill *M. tuberculosis*. An unexploited enzyme in the pathway that has been targeted by one the most successful antibiotics in human clinical use, namely the β-lactams, has been characterized and its role identified. Therefore, an agent that inhibits the L,D-transpeptidase enzyme or a regimen containing a combination of L,D-transpeptidase inhibitor and a β-lactam may be able to kill *M. tuberculosis* by comprehensively destroying the peptidoglycan layer. As the peptidoglycan layer is a vital structure of the bacterial cell wall, insight and applications resulting from studies in *M. tuberculosis* is likely broadly applicable to other bacteria.

The following examples are intended to illustrate but not limit the invention.

Example 1

Production and Purification of Recombinant $Ldt_{Mt2}$

A portion of the $ltd_{Mt2}$ gene was amplified with primers 5'-TT<u>TTCATGA</u>T-CGCCGATCTGCTGGTGC-3' (SEQ ID NO:2) and 5'-TT<u>GGATCCC</u>GCCTTGGCGTTACCGGC-3' (SEQ ID NO:3), digested with BspHI plus BamHI (underlined) and cloned into pET2818. The resulting plasmid, encodes a fusion protein consisting of a methionine specified by the ATG initiation codon of pET2818, residues 55 to 408 of LdtMt2, and a C-terminal polyhistidine tag with the sequence $GSH_6$ (SEQ ID NO:4). *E. coli* BL21(DE3) harboring pREP4GroESL and pET2818QldtMt2 was grown at 37° C. to an $OD_{600}$ of 0.5 in 3 L of brain heart infusion broth containing 150 µg/ml ampicillin. Expression was induced by adding Isopropyl-D-thiogalactopyranoside to a final concentration of 0.5 mM and incubating the cultures for 17 hours at 16° C. $Ldt_{Mt2}$ was purified from a clarified lysate by affinity chromatography on $Ni^{2+}$-nitrilotriacetate-agarose resin (Qiagen GmbH, Germany) followed by anion exchange chromatography (MonoQ HR5/5, Amersham Pharmacia Biotech) with an NaCl gradient in 50 mM Tris-HCl pH 8.5. An additional size exclusion chromatography was performed on a Superdex HRI0/30 column (Amersham Pharmacia Biotech) equilibrated with 50 mM Tris-HCl (pH 7.5) containing 300 mM NaCl at a flow rate of 0.5 ml/minute. The protein was concentrated by ultrafiltration (Amicon Ultra-4 centrifugal filter devices, Millipore) and stored at −20° C. in the same buffer supplemented with 20% glycerol.

Example 2

L, D-Transpeptidase Assays

We purified disaccharide-tetrapeptide containing amidated meso-diaminopimelic acid (GlcNAc-MurNAc-L-$Ala^1$-D-$iGln^2$-meso$Dap_{NH2}^3$-D-$Ala^4$) (SEQ ID NO:5) from *C. jeikeium* strain CIP103337 and determined the concentration after acid hydrolysis. In vitro formation of muropeptide dimers was tested in 10 µL of 50 mM Tris-HCl (pH 7.5) containing 300 mM NaCl, 5 µM $Ldt_{Mt2}$, and 280 µM disaccharide-tetrapeptide. The reaction mixture was incubated for two hours at 37° C. the resulting muropeptides were analyzed by nanoelectrospray tandem mass spectrometry using $N_2$ as the collision gas.

Example 3

Bacterial Strains and Culture Conditions

*M. tuberculosis* CDC1551, a clinical isolate, was used as the host strain and a transposon insertion mutant in MT2594 (ldtMt2::Tn) was generated, isolated and characterized as described in Lamichhane et al., PNAS, 2003, 100(12): 7213-7218. This mutant carries a Himar1 transposon insertion at +872 base from the putative translation start site of the gene. The complemented strain was generated by transforming the mutant with pGS202_2594. This is a single copy integrating plasmid based on pMH94 backbone, which was modified into a GATEWAY compatible destination vector (Invitrogen) by inserting attL1 and attL2 sites. A wild-type copy of MT2594 along with its promoter was cloned into this destination vector pGS202 to generate pGS202_2594. Genotypes of the strains were verified by Southern blotting. For in vitro growth, Middlebrook 7H9 liquid medium supplemented with 0.2% glycerol, 0.05% Tween-80, 10% vol/vol oleic acid-albumin-dextrose-catalase (OADC) and 50 µg/ml cyclohex-imide was used. Middlebrook 7H11 solid medium (Becton-Dickinson) was used for enumerating colony forming units (CFU) in in vitro and in vivo growth studies.

Example 4

Peptidoglycan Structure Analysis

*M. tuberculosis* MT2594 was grown at 37° C. with shaking in Dubos broth (Difco) supplemented with 10% (vol/vol) of OADC (Becton Dickinson. A 10-day preculture of 25 ml was used to inoculate 300 ml of the growth medium. After 3 weeks of incubation, bacteria were collected by centrifugation, inactivated by heat (96° C. for 30 minutes), resuspended in 6 ml of 10 mM phosphate buffer (pH 7.0), and disrupted with glass beads (150-212 µm; 5 g/5 ml, weight/vol) for 16 hours at 4° C. in a cell disintegrator (The Mickle Laboratory Engineering Co, Gromshall, United Kingdom). Cell-wall was collected by centrifugation (15,000×g for 15 minutes at 4° C.) and the peptidoglycan was extracted with 8% boiling SDS, and washed three times with water. Peptidoglycan was treated with proteases, digested with mutanolysin and lysozyme, as previously described in Arbeloa et al., J. Biol. Chem., 2004, 279: 41546-41556. The resulting muropeptides were treated with ammonium hydroxide to cleave the ether link internal to MurNAc. Peptidoglycan fragments were purified by rp-HPLC and analyzed by mass spectrometry.

Example 5

Growth and Virulence Analysis in Mice

Four to five week old, female Balb/c mice (Charles River Laboratories) were used to study in vivo virulence of the strains and their susceptibility to drugs. Mice were infected with a log phase culture of wildtype *M. tuberculosis*, or ldtMt2::Tn or the complemented strain in an aerosol chamber. For assessing in vivo growth of each strain, four mice per group were sacrificed at days 1, 7, 14, 28, 56 and 98 following infection, lungs and spleen were obtained, homogenized and appropriate dilutions were cultured on Middlebrook 7H11 medium to determine colony forming units (CFU). Twelve mice for each infection group were allocated to assess virulence of each strain. For this, median-survival-time for each mouse surviving following infection was determined. Protocols for experiments involving mice were approved by Johns Hopkins University Animal Care and Use Committee.

Example 6

Extraction and Analysis of Lipids

Total lipids were isolated from *M. tuberculosis* wild type, ldtMt2::Tn and complemented strains as described in Besra, *Mycobacteria* Protocols, (Humana Press, Totowa, 1998, (eds. Parish, T. & Stoker, N. G.): 91-107. 100 ml of mycobacterial cultures grown in Middlebrook 7H9 to an OD of 1.5 were harvested and autoclaved. Lipids were extracted by adding 2 ml of methanol: 0.3% NaCl (100:10) and 1 ml of petroleum ether. The upper petroleum ether layer was removed after centrifugation and dried. 250 µl of dicholormethane was added to the fraction containing apolar lipids. The lipids were analyzed using three different solvent systems on two-dimensional thin layer chromatography (TLC). For solvent A, petroleum ether:ethyl acetate (98:2) was used as the first dimension and petroleum ether:acetone (98:2) was used as the second dimension. Similarly solvent system B comprised of choloroform:methanol (96:4) and toluene:acetone (80:20) and solvent C of chloroform:methanol:water (87:12:1) and chloroform:acetone:methanol:water (42:53:2:3). All TLC plates were developed in 5% phosphomolybdic acid and charred at 100° C.

Example 7

Inhibition of LdtMt2 by β-Lactams $Ldt_{Mt2}$ (5 µM) was pre-incubated for 20 minutes at 37° C. with ampicillin (Bristol-Myers), ceftriaxone (Roche Apphed Science), and imipenem (Merck Sharpe and Dhome-Chibret) in 50 mM Tris-HCl (pH 7.5) containing 300 mM NaCl. The L,D-transpeptidation reaction was started by the addition of the disaccharide-tetrapeptide (final concentration 280 µM) and allowed to proceed for 2 hours at 37° C. The reaction mixture was dialyzed against water for 30 minutes. The reaction products were detected by mass spectrometry. The formation of enzyme-drug adduct was tested by incubating $Ldt_{Mt2}$ (5 µM) with ampicillin, ceftriaxone, imipenem, meropenem (AstraZeneca) and ertapenem (Merck Sharpe and Ohome-Chibret) at 50 µM for 1 hour at 37° C. in 50 mM Tris-HCl (pH 7.5) containing 300 mM NaCl. The reaction mixture was dialyzed against water for 30 minutes and the average mass of proteins and protein β-lactam adducts were determined as described in Mainardi et al., 2007, J. Biol. Chem., 282: 30414-30422.

Example 8

Drug Susceptibility Testing in Mice

In vitro minimum inhibitory concentrations for amoxicillin/clavulanate, imipenem (Merck), isoniazid (Sigma) and cycloserine (Sigma) were determined using the broth dilution method. Augmentin (GlaxoSmithKline), a preparation containing amoxicillin and clavulanate was used as *M. tuberculosis* contains β-lactamases. For this, $10^5$ *M. tuberculosis* bacilli were inoculated into 2.5 ml of 7H9 broth and drugs at different concentrations were added. The cultures were incubated at 37° C. and evaluated for growth by visual inspection of the pellet size at 7 and 14 days. Samples with diminished growth, compared to no-drug control, were further assessed by plating to determine CFU. Four to five week old, female Balb/C mice were used for in vivo assessment of susceptibility of *M. tuberculosis* lacking $Ldt_{Mt2}$ to amoxicillin. Two groups of mice, 48 per group, were infected with aerosolized cultures of either wild-type *M. tuberculosis* or $Idt_{mt2}$::Tn. Mice from each group were divided into 4 sub-groups of 12 mice each and daily treatment was initiated at 2 weeks following infection. Each sub-group received either 25 mg/kg isoniazid, or 200 mg/kg amoxicillin and 50 mg/kg clavulanate, or no drug at all. The drugs were delivered in 200 µl solutions by oral gavage. Four mice from each treatment sub-group were sacrificed at 1, 2 and 4 weeks following start of therapy. Lungs and spleen were obtained, homogenized in 1 ml of 1×PBS and CFU in each organ was determined by plating appropriate dilutions of the homogenates on Middlebrook 7H11 selective plates.

Example 9

Expression of $Ldt_{Mt2}$ and Paralogs

Total RNA was isolated from wild-type *M. tuberculosis* CDC1551 grown in Middlebrook 7H9 medium at optical densities (OD600 nm) of 0.2, 0.5, 0.8, 0.9, 1.9, 3.0, 2 days after 3.0, and 3 days after clumping using Trizol (Invitrogen). Gene specific primers for MT2594, MT0125, MT0202, MT0501, MT1477 and SigA were used for reverse transcription (RT) using superscript III (Invitrogen). The resulting cDNAs were amplified and quantified using qPCR (Bio-Rad). SigA, whose expression in known to be constant throughout the growth phases was used as a control against which all cycle threshold values were normalized. The RT and qPCR were repeated for statistical validation of the data.

Although the invention has been described with reference to the above example, it will be understood that modifications and variations are encompassed within the spirit and scope of the invention. Accordingly, the invention is limited only by the following claims.

What is claimed is:

1. A method of identifying a $Ldt_{Mt2}$ L, D-transpeptidase enzyme ligand, comprising:
   contacting $Ldt_{Mt2}$ L, D-transpeptidase having a first mass with a test agent in vitro; and
   detecting formation of an $Ldt_{Mt2}$ L, D-transpeptidase-adduct by mass spectrometry, wherein the formation of an adduct is evidenced by an overall increase in the first mass of the enzyme, thereby identifying a $Ldt_{Mt2}$ L, D-transpeptidase enzyme ligand.

2. The method of claim 1, wherein the $Ldt_{Mt2}$ L, D-transpeptidase enzyme is in a mycobacterial cell.

3. The method of claim 1, wherein the test agent is selected from the group consisting of β-lactamase inhibitors, penicillins, aminoglycosides, sulfonamides, tetracyclines, macrolides, β-lactams, cephalosporins, monobactams, fluoroquinolones and carbapenems.

4. The method of claim 2, wherein the mycobacterial cells is a *Mycobacterium tuberculosis* cell.

5. The method of claim 2, wherein the mycobacterial cell causes a mycobacterial infection in a host.

6. The method of claim 5, wherein the mycobacterial infection is tuberculosis.

7. The method of claim 5, wherein the mycobacterial infection is chronic phase tuberculosis.

8. The method of claim 1, wherein the L, D-transpeptidase enzyme is encoded by Mycobacterium tuberculosis ldtB gene having accession number Rv2518c.

9. The method of claim 2, wherein $Ldt_{Mt2}$ L, D-transpeptidase enzyme activity is detected by determination of colony forming units before and after contact with the test agent.

10. The method of claim 1, wherein the first mass of the enzyme is detected in the absence of the test agent.

* * * * *

SEQUENCE LISTING

```
<160> NUMBER OF SEQ ID NOS: 5

<210> SEQ ID NO 1
<211> LENGTH: 4
<212> TYPE: PRT
<213> ORGANISM: Artificial Sequence
<220> FEATURE:
<223> OTHER INFORMATION: Synthetic construct: invariant motif

<400> SEQUENCE: 1

Ser His Gly Cys
1

<210> SEQ ID NO 2
<211> LENGTH: 27
<212> TYPE: DNA
<213> ORGANISM: Artificial Sequence
<220> FEATURE:
<223> OTHER INFORMATION: Primer

<400> SEQUENCE: 2
ttttcatgat cgccgatctg ctggtgc                                          27

<210> SEQ ID NO 3
<211> LENGTH: 26
<212> TYPE: DNA
<213> ORGANISM: Artificial Sequence
<220> FEATURE:
<223> OTHER INFORMATION: Primer

<400> SEQUENCE: 3
ttggatcccg ccttggcgtt accggc                                           26

<210> SEQ ID NO 4
<211> LENGTH: 8
<212> TYPE: PRT
<213> ORGANISM: Artificial Sequence
<220> FEATURE:
<223> OTHER INFORMATION: Synthetic construct

<400> SEQUENCE: 4

Gly Ser His His His His His His
1               5

<210> SEQ ID NO 5
<211> LENGTH: 4
<212> TYPE: PRT
<213> ORGANISM: Corynebacterium jeikeium
<220> FEATURE:
<221> NAME/KEY: MISC_FEATURE
<222> LOCATION: (2)..(2)
<223> OTHER INFORMATION: Xaa is Isoglutamine (iGln)
<220> FEATURE:
<221> NAME/KEY: MISC_FEATURE
<222> LOCATION: (3)..(3)
```

```
<223> OTHER INFORMATION: Xaa is meso-2,6-diaminoheptanediamide (amidated
      meso-diaminopimelic acid)

<400> SEQUENCE: 5

Ala Xaa Xaa Ala
1
```